US010335140B2

(12) United States Patent
Baird et al.

(10) Patent No.: US 10,335,140 B2
(45) Date of Patent: Jul. 2, 2019

(54) MENISCAL REPAIR SYSTEMS AND METHODS

(71) Applicant: Cayenne Medical, Inc., Scottsdale, AZ (US)

(72) Inventors: Kevin N. Baird, Phoenix, AZ (US); Nicanor A. Domingo, Santa Clara, CA (US); Hoang Nguyen, Litchfield Park, AZ (US); Brad Niese, Gilbert, AZ (US); Melissa Toman, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 253 days.

(21) Appl. No.: 15/273,429

(22) Filed: Sep. 22, 2016

(65) Prior Publication Data

US 2017/0100119 A1 Apr. 13, 2017

Related U.S. Application Data

(62) Division of application No. 12/771,455, filed on Apr. 30, 2010, now Pat. No. 9,486,208.
(Continued)

(51) Int. Cl.
*A61B 17/00* (2006.01)
*A61B 17/04* (2006.01)
(Continued)

(52) U.S. Cl.
CPC ...... *A61B 17/0469* (2013.01); *A61B 17/0482* (2013.01); *A61B 17/0491* (2013.01);
(Continued)

(58) Field of Classification Search
CPC ............ A61B 17/0469; A61B 17/0482; A61B 17/0491; A61B 207/00367;
(Continued)

(56) References Cited

U.S. PATENT DOCUMENTS 4,493,323 A * 1/1985 Albright ............ A61B 17/0469
606/144
5,178,628 A 1/1993 Otsuka et al.
(Continued)

FOREIGN PATENT DOCUMENTS

JP 2006025932 A 2/2006

OTHER PUBLICATIONS

"U.S. Appl. No. 12/771,455, Notice of Allowance dated Jun. 27, 2016", 9 pgs.
(Continued)

*Primary Examiner* — Jocelin C Tanner
(74) *Attorney, Agent, or Firm* — Schwegman Lundberg & Woessner, P.A.

(57) ABSTRACT

A device for repairing a tear in a portion of tissue comprises a proximal actuator portion, a transfer needle extending distally from the proximal actuator portion and a catch needle extending distally from the proximal actuator portion. A suture needle is disposed in the transfer needle, and is extendable from the transfer needle toward the catch needle and retractable from the catch needle toward the transfer needle. An extendable catch plunger is disposed in the catch needle for capturing suture therein when it is transferred from the transfer needle. A retractable insertion sheath is provided for covering the transfer needle and the catch needle when the device is inserted into a procedural site. A depth limiting apparatus limits the depth of insertion of the needle into the procedural site.

18 Claims, 13 Drawing Sheets

Related U.S. Application Data

(60) Provisional application No. 61/174,953, filed on May 1, 2009.

(51) Int. Cl.
*A61B 17/06* (2006.01)
*A61B 90/00* (2016.01)

(52) U.S. Cl.
CPC ........... *A61B 2017/00367* (2013.01); *A61B 2017/00845* (2013.01); *A61B 2017/0472* (2013.01); *A61B 2017/0477* (2013.01); *A61B 2017/0496* (2013.01); *A61B 2017/061* (2013.01); *A61B 2017/06042* (2013.01); *A61B 2017/06052* (2013.01); *A61B 2017/06095* (2013.01); *A61B 2090/036* (2016.02); *A61B 2090/062* (2016.02); *A61B 2090/064* (2016.02); *A61B 2090/0811* (2016.02)

(58) Field of Classification Search
CPC ...... A61B 207/00845; A61B 207/0472; A61B 207/0477; A61B 207/0496; A61B 207/06042; A61B 207/06052; A61B 207/06095; A61B 207/061; A61B 2090/036; A61B 2090/062; A61B 2090/064; A61B 2090/0811
See application file for complete search history.

(56) References Cited

U.S. PATENT DOCUMENTS

| | | | |
|---|---|---|---|
| 5,895,395 A * | 4/1999 | Yeung | A61B 17/0469 606/139 |
| 6,162,209 A | 12/2000 | Gobron et al. | |
| 6,638,286 B1 | 10/2003 | Burbank et al. | |
| 6,679,895 B1 | 1/2004 | Sancoff et al. | |
| 7,326,222 B2 * | 2/2008 | Dreyfuss | A61B 17/0469 606/103 |
| 9,486,208 B2 | 11/2016 | Baird et al. | |
| 2003/0208210 A1 | 11/2003 | Dreyfuss et al. | |
| 2005/0187519 A1 * | 8/2005 | Harris | A61M 25/0068 604/117 |
| 2005/0288690 A1 | 12/2005 | Bourque et al. | |
| 2008/0091219 A1 * | 4/2008 | Marshall | A61B 17/0469 606/144 |
| 2009/0143806 A1 * | 6/2009 | Witt | A61B 17/320092 606/169 |
| 2010/0305583 A1 | 12/2010 | Baird et al. | |

OTHER PUBLICATIONS

"European Application Serial No. 10770436.3, Communication Pursuant to Article 94(3) EPC dated Jan. 23, 2017", 5 pgs.

"European Application Serial No. 10770436.3, Communication Pursuant to Article 94(3) EPC dated Apr. 13, 2016", 4 pgs.

"European Application Serial No. 10770436.3, Extended European Search Report dated Apr. 17, 2015", 10 pgs.

"European Application Serial No. 10770436.3, Response filed Jun. 1, 2017 to Communication Pursuant to Article 94(3) EPC dated Jan. 23, 2017", 14 pgs.

"European Application Serial No. 10770436.3, Response filed Jun. 22, 2012 to Communication pursuant to Rules 161(1) and 162 EPC dated Dec. 29, 2011", 5 pgs.

"European Application Serial No. 10770436.3, Response filed Oct. 13, 2016 to Communication Pursuant to Article 94(3) EPC dated Apr. 13, 2016", 12 pgs.

"European Application Serial No. 10770436.3, Response filed Nov. 17, 2015 to Extended European Search Report dated Apr. 17, 2015", 8 pgs.

"Indian Application Serial No. 7961/CHENP/2011 , Office Action dated Nov. 12, 2018", w/ English translation, 7 pgs.

* cited by examiner

MENISCAL REPAIR SYSTEMS AND METHODS

This application is a divisional under 35 U.S.C. 120 of co-pending application Ser. No. 12/771,455, filed on Apr. 30, 2012 and entitled Meniscal Repair Systems and Methods, now allowed, which in turn claims the benefit under 35 U.S.C. 119(e) of the filing date of Provisional U.S. Application Ser. No. 61/174,953, entitled Arthroscopic Meniscal Repair System and Methods, filed on May 1, 2009. Both of these prior applications are expressly incorporated herein by reference, in their entirety.

The present application is also related to prior commonly assigned U.S. application Ser. No. 12/398,100, filed on Mar. 4, 2009, and entitled Arthroscopic Meniscal Repair System and Methods, now U.S. Pat. No. 8,814,885, issued on Aug. 26, 2014, as well as to prior commonly assigned U.S. application Ser. No. 12/603,232, filed on Oct. 21, 2009, and entitled Meniscal Repair Systems and Methods, now U.S. Pat. No. 8,177,795, issued on May 15, 2012. These prior related patents are also herein expressly incorporated by reference, in their entirety.

BACKGROUND OF THE INVENTION

The present invention relates to surgical repair of meniscal tears, and more particularly to a unique arthroscopic handheld device and methods for repairing meniscal tears by passing suture within the meniscus through the tear.

There are two menisci in each knee, the medial meniscus, and the lateral meniscus, each of which comprises fibrocartilage. The menisci protect the articular cartilage on the surfaces of the femur and the tibia. Historically, torn portions of a meniscus were simply surgically removed. However, over time, it has become known in the field that removing substantial portions of the meniscus often accelerates the onset of osteoarthritis and other complications which develop when the shock absorbing meniscuses in the knee are absent. Most tears of the meniscus do not heal on their own, because of a very limited blood supply, but, using modem techniques, many tears can be surgically repaired, thus avoiding the need to remove meniscal portions.

Current meniscal repair methods and devices include both open surgical and arthroscopic techniques. Some repair approaches utilize suture only, others utilize anchors only, while still others are hybrid techniques which employ both suture and anchor devices.

Traditional prior art arthroscopic meniscal repair methods begin with a complicated suture only, "inside outside" technique. These techniques involve several access ports into the surgical site, and several instrument exchanges during the procedure, increasing surgical time and complexity. Because of this, the required surgical skill to effectively execute these arthroscopic procedures is quite high. A benefit to these conventional methods is that only suture is left behind at the procedural site, thus eliminating the risk of loose bodies in the knee space as well as abrasion to the articular cartilage from hard plastic or metal implants.

Another surgical technique that has developed involves a plastic implant with no suture. The implant has a dart shape to it with barbs that, when inserted into the meniscus, resist backing out. A benefit to this type of technology is that it avoids the need for numerous ports or instrument exchanges. This is a much easier method to execute than the suture-only method discussed above, but its downside is that it leaves a plastic head in the articular space, which causes abrasion to the femoral condyle articular cartilage.

Still another conventional meniscal repair technique that has been developed is a hybrid involving both an implant and suture. The benefit to this hybrid approach is that the practitioner gains the ease of the implant technique, as discussed above, but there is no exposed plastic implant in the articular space. The downside risk that still exists with this approach is that of a hard plastic loose body remaining at the procedural site. Should some sort of failure occur, the hard plastic implant may come loose and cause damage in the articular space.

Current devices on the market such as the FAST-FIX sold by Smith and Nephew use a disposable depth limiter that needs to be cut prior to inserting into the joint space and to prevent injury to neurovascular structures. The device also requires a separate cannula to insert the device into the joint space.

Other devices such as the Biomet MAXFIRE require several different reusable depth limiting cannula to access the joint space and prevent injury to neurovascular structures.

What is needed, therefore, is an arthroscopic meniscal repair system and technique which combines the ease of the prior art implant procedures, while eliminating the risk that comes with a hard plastic implant.

SUMMARY OF THE INVENTION

The present invention comprises an all suture approach having the ease of a single working portal, a pre-tied knot, and a single handed device that includes a pre-tied knot. It duplicates the ease of the implant procedures discussed above, but eliminates the risk that comes with a hard plastic implant.

The inventive device passes suture from one needle to another, while both are positioned inside of the meniscus (intra-meniscal) as well as outside of the knee capsule. The suture has a pre-tied knot which is then utilized to draw the unstable portion of the torn meniscus back into contact with the stable portion, thereby stabilizing the meniscus and promoting healing.

More particularly, there is provided a device for repairing a tear in a portion of tissue, which comprises a proximal actuator portion, a transfer needle extending distally from the proximal actuator portion and having a distal tip for piercing tissue, and a catch needle extending distally from the proximal actuator portion and having a distal tip for piercing tissue. A suture needle is disposed in the transfer needle, and is extendable from the transfer needle toward the catch needle and retractable from the catch needle toward the transfer needle. An extendable catch plunger is disposed in the catch needle for capturing suture therein when it is transferred from the transfer needle. A retractable insertion sheath is provided for covering the transfer needle and the catch needle when the device is inserted into a procedural site. The proximal actuator portion comprises an insertion sheath actuator for retracting the insertion sheath, a suture needle advancement actuator for advancing and retracting the suture needle, and a catch plunger release mechanism for releasing the catch plunger for travel distally. The suture needle advancement actuator advantageously has an actuation position which also actuates the catch plunger release mechanism. In a preferred embodiment, this actuation position is when the actuator, which preferably comprises a lever, is fully depressed.

The transfer needle comprises a window disposed laterally thereon, through which the suture needle is extended or retracted. The catch needle, similarly, comprises a window disposed laterally thereon, through which the suture needle is extended or retracted. A second window is disposed on the catch needle on a side opposed to the side on which the first window is disposed, through which a distal end of the catch needle extends when the suture needle is fully extended into the catch needle.

The suture needle is sufficiently flexible that it attains a straightened configuration when housed within the transfer needle, and acquires a bend which assists in directing it toward the catch needle when the distal end of the suture needle extends out of the transfer needle.

An advantageous feature of the present invention is the inclusion of a depth limiting apparatus for limiting the depth of insertion of the needles into the procedural site. In one embodiment, the depth limiting apparatus comprises a depth gauge disposed on the proximal actuator portion, which preferably comprises a handle. In this embodiment, the insertion sheath actuator comprises a button which slides axially along a slot in the proximal actuator portion, and the depth gauge comprises graduated markings disposed along the slot, so that a practitioner can retract the sheath by sliding the insertion sheath actuator button a predetermined distance along the slot to control the depth of insertion of the device.

In an alternative embodiment, the depth limiting apparatus comprises a force feedback unit disposed on a distal end of the device. The force feedback unit preferably comprises a compression force element disposed on a distal end of one of the needles. The force feedback unit is preferably disposed on the shorter one of the needles, which is, in the current embodiments, the transfer needle. The compression force element comprises a plunger in the illustrated embodiment, though it may also comprise an electronic sensor, such as a strain gauge, or other suitable electronic or mechanical force sensing device. In this embodiment, the force feedback unit is coupled with a depth limiter which is movable distally along the device, responsive to a reduction of force on the force feedback unit.

In some embodiments, it may be advantageous for each of the transfer needle and the catch needle to be curved, rather than straight, along their respective lengths.

In another aspect of the invention, there is provided a device for repairing a tear in a portion of tissue, which comprises a proximal actuator portion, a needle for dispensing suture into the tissue to be repaired, a retractable insertion sheath for covering the needle when the device is inserted into a procedural site, and a depth limiting apparatus for limiting the depth of insertion of the needle into the procedural site. The proximal actuator portion, which preferably comprises a handle, also comprises an insertion sheath actuator for retracting the insertion sheath.

In one embodiment, the depth limiting apparatus comprises a depth gauge disposed on the proximal actuator portion, which preferably comprises a handle. In this embodiment, the insertion sheath actuator comprises a button which slides axially along a slot in the proximal actuator portion, and the depth gauge comprises graduated markings disposed along the slot, so that a practitioner can retract the sheath by sliding the insertion sheath actuator button a predetermined distance along the slot to control the depth of insertion of the device.

In an alternative embodiment, the depth limiting apparatus comprises a force feedback unit disposed on a distal end of the device. The force feedback unit preferably comprises a compression force element disposed on a distal end of the needle. The compression force element comprises a plunger in the illustrated embodiment, though it may also comprise an electronic sensor, such as a strain gauge, or other suitable electronic or mechanical force sensing device. In this embodiment, the force feedback unit is coupled with a depth limiter which is movable distally along the device, responsive to a reduction of force on the force feedback unit.

In still another aspect of the invention, there is disclosed a method for repairing a tear in a portion of tissue, which comprises a step of inserting a device comprising a proximal actuator portion and a distal needle portion into a procedural site. A sheath covering the needle is retracted proximally to expose the distal end of the needle, followed by a step of advancing the needle into the tissue to be repaired, so that a distal end of the needle is disposed beyond the tear, until a depth limiting structure prevents further advancement of the needle. Further steps include creating a suture loop in the tissue to repair the tear, withdrawing the needle proximally from the procedural site, and using a pre-tied knot to cinch the suture loop and thereby repair the tear.

The advancing step of the disclosed method comprises advancing a pair of needles into the tissue to be repaired, and the suture loop creating step is performed by dispensing suture from one of the needles into a second of the needles, and then releasing a catch plunger to move distally and clamp the suture to retain it in the second needle.

The depth limiting structure comprises a distal end of the sheath, and, in one disclosed method, the sheath retracting step includes a step of determining a distance through which the sheath is retracted by consulting a depth gauge disposed on the proximal actuator portion. In an alternative disclosed method, the depth limiting structure comprises a depth limiter which is movable distally along the device toward the tissue to be repaired responsive to a release of force on a force feedback unit disposed on a distal end of the needle.

In still another aspect of the invention, there is provided a device for repairing a tear in a portion of tissue, which comprises a proximal actuator portion, a transfer needle extending distally from the proximal actuator portion and having a distal tip for piercing tissue, a catch needle extending distally from the proximal actuator portion and having a distal tip for piercing tissue, and a suture needle disposed within a lumen in the transfer needle. The suture needle is extendable from the transfer needle toward the catch needle and retractable from the catch needle toward the transfer needle. A window is disposed on the transfer needle, through which the suture needle may be deployed. The transfer needle window has two substantially parallel sides and a bearing surface which is disposed substantially perpendicularly to a path of the suture needle as the suture needle traverses into and out of the window. Advantageously, the window has a length that is shorter than required to permit free translation of the suture needle into and out of the window, so that an interfering contact is created between a first surface of the suture needle and the edge of the transfer needle window.

The suture needle comprises a second surface thereof which is substantially flat and on an opposing side of the suture needle relative to the first surface. An advantage of the present invention is that, because of this construction, the interfering contact between the first suture needle surface and the edge of the transfer needle window causes the flat second suture needle surface against the transfer needle bearing surface.

A suture catch window is provided in the catch needle for receiving the suture needle into the catch needle. The suture needle comprises angled surfaces extending from a distal tip thereof, and the suture catch window also comprises angled surfaces. The suture needle angled surfaces and the suture catch window angled surfaces are configured to correspond to one another so that the suture needle slides and ramps along the suture catch window angled surfaces to assist in guiding the suture needle into and out of the suture catch window.

An extendable catch plunger is disposed in the catch needle for capturing suture therein when it is transferred from the transfer needle, wherein the catch plunger comprises an angled distal surface which is configured to mate with a corresponding one of the angled suture needle surfaces. Preferably, a second window is disposed on the catch needle on a side opposed to the side on which the first window is disposed, through which a distal end of the suture needle extends when the suture needle is fully extended into the catch needle.

The inventive device also comprises a retractable insertion sheath for covering the transfer needle and the catch needle when the device is inserted into a procedural site. The proximal actuator portion comprises an insertion sheath actuator for retracting and advancing the insertion sheath. A depth limiting apparatus is provided for limiting the depth of insertion of the needles into the procedural site, which is integrated with the insertion sheath actuator. The depth limiting apparatus comprises a depth gauge disposed on the proximal actuator portion. The insertion sheath actuator comprises a button which slides axially along a slot in said proximal actuator portion, with the depth gauge comprising graduated numbered markings disposed along the slot, so that a practitioner can retract the sheath by sliding the insertion sheath actuator button to a selected position along the slot to control the depth of insertion of the device, between a locked forward configuration and a locked backward configuration.

Another innovative feature of the present invention is a cleat disposed within the proximal actuator portion, which is attached to a length of suture extending from the proximal actuator portion and having a pre-tied knot thereon. The cleat is configured to selectively apply tension to the suture. Prior to deployment, the pre-tied knot is disposed beneath the sheath and there is a substantial length of slack suture within the proximal actuator portion. The pre-tied knot is deployed to secure the tissue repair by pulling the device proximally away from the procedural site, so that the pre-tied knot slides distally over the needles and length of suture, with the slack suture attached to the cleat simultaneously being reduced.

In a preferred embodiment, the suture needle is comprised of nitinol, and the transfer needle is comprised of stainless steel, though other suitable biocompatible materials may, of course, be used. Preferably, to reduce friction associated with moving the suture needle back and forth between the transfer needle and the catch needle, an oxide layer infused with tungsten disulfide is formed between the suture needle and the transfer needle.

In another aspect of the invention, there is provided a device for repairing a tear in a portion of tissue, which comprises a proximal actuator portion, a transfer needle extending distally from the proximal actuator portion and having a distal tip for piercing tissue, a catch needle extending distally from the proximal actuator portion and having a distal tip for piercing tissue, and a suture needle disposed within a lumen in the transfer needle. The suture needle is extendable from the transfer needle toward the catch needle and is retractable from the catch needle toward the transfer needle. An oxide layer infused with tungsten disulfide is formed between the suture needle and the transfer needle to reduce friction therebetween. In one preferred embodiment, the suture needle is comprised of nitinol and the transfer needle is comprised of stainless steel.

In yet another aspect of the invention, there is provided a device for repairing a tear in a portion of tissue, which comprises a proximal actuator portion, a needle for dispensing suture into the tissue to be repaired, a retractable insertion sheath for covering the needle when the device is inserted into a procedural site, and a cleat disposed within the proximal actuator portion. The cleat is attached to a length of suture extending from the proximal actuator portion, which has a pre-tied knot thereon, the cleat being configured to selectively apply tension to the suture. Prior to deployment, the pre-tied knot is disposed beneath the sheath and there is a substantial length of slack suture within the proximal actuator portion. For deployment, the pre-tied knot slides distally over the needles and length of suture when the device is pulled proximally away from the procedural site, with the slack suture attached to the cleat simultaneously being reduced.

In still another aspect of the invention, there is disclosed a method for repairing a tear in a portion of tissue, which comprises steps of inserting a device comprising a proximal actuator portion and a distal needle portion into a procedural site, retracting a sheath covering the needle proximally to expose the distal end of the needle, advancing the needle into the tissue to be repaired, and creating a suture loop in the tissue to repair the tear. The needle is then withdrawn proximally from the procedural site. The withdrawing action is used to simultaneously move a pre-tied knot distally along the suture to the site of the repair, and the suture is tensioned using a cleat within the proximal actuator portion to cinch the suture loop and thereby complete the tissue repair.

The invention, together with additional features and advantages thereof, may best be understood by reference to the following description taken in conjunction with the accompanying illustrative drawing.

DESCRIPTION OF THE PREFERRED EMBODIMENT

Figure 1:
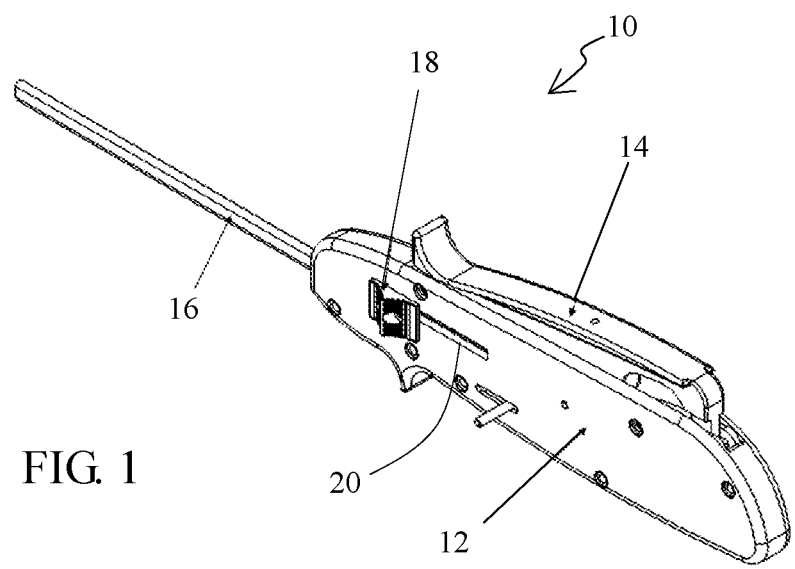
FIG. 1 is an isometric view showing one embodiment of a meniscal repair device constructed in accordance with the principles of the present invention.

Referring now more particularly to the drawings, there is shown in FIG. 1 an embodiment of a meniscal repair device 10 constructed in accordance with the principles of the present invention. The device 10 comprises a handle 12 which has a suture needle advancement lever 14. Distally of the handle 12 is provided a depth limiter/insertion sheath 16. A depth limiter/insertion sheath actuation button 18 is disposed on the handle 12.

Figure 2:
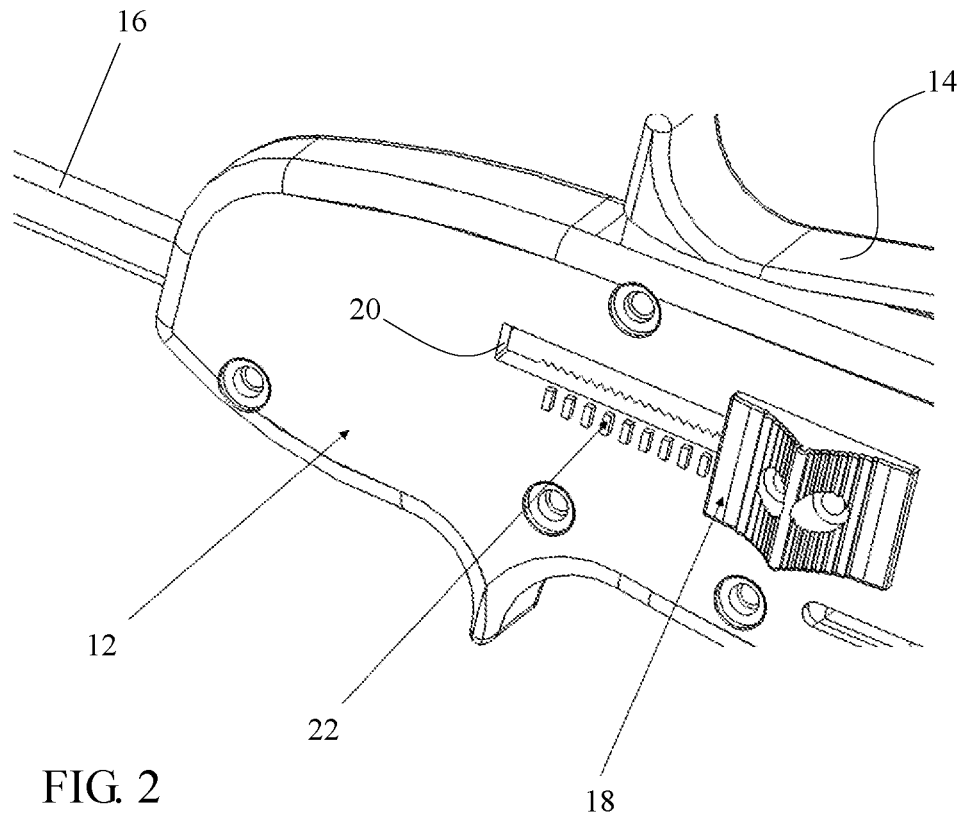
FIG. 2 is an isometric enlarged view of portions of the handle of the meniscal repair device of FIG. 1.
Figure 7:
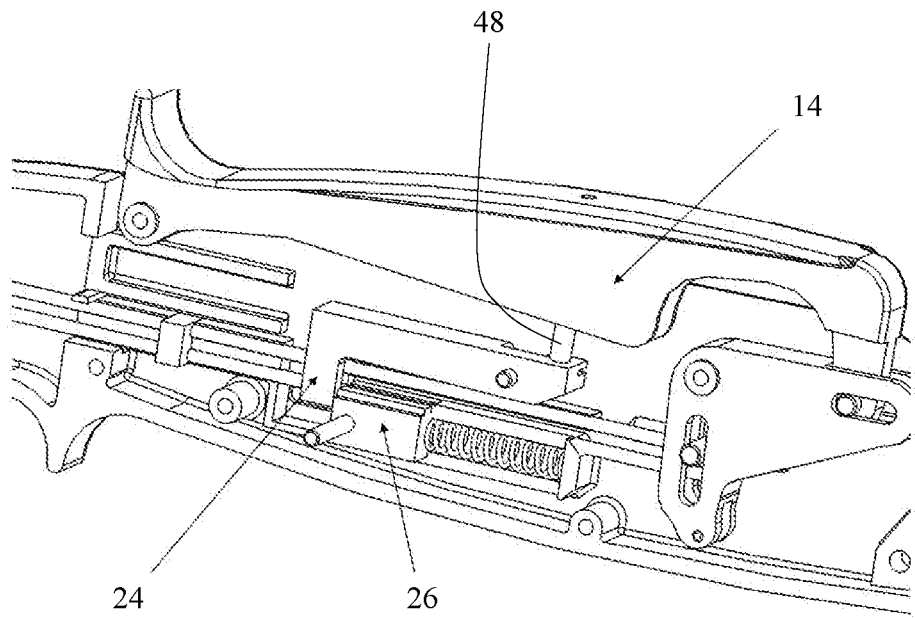
FIG. 7 is an enlarged isometric view of the handle of the meniscal repair device of the present invention, with the cover removed to show the interior construction thereof.

Now with reference to FIGS. 2 and 7, in addition to FIG. 1, additional constructional details of the handle 12 are illustrated. As shown particularly in FIG. 2, the depth limiter/insertion sheath actuation button 18 travels axially within a slot 20. A depth gauge 22 is provided for purposes which will be described below. In FIG. 7, wherein the cover of the handle has been removed to reveal the internal construction of the handle 12, it can be seen that a piston retention lever 24 and a catch spring piston 26 are disposed therein.

Figure 6:
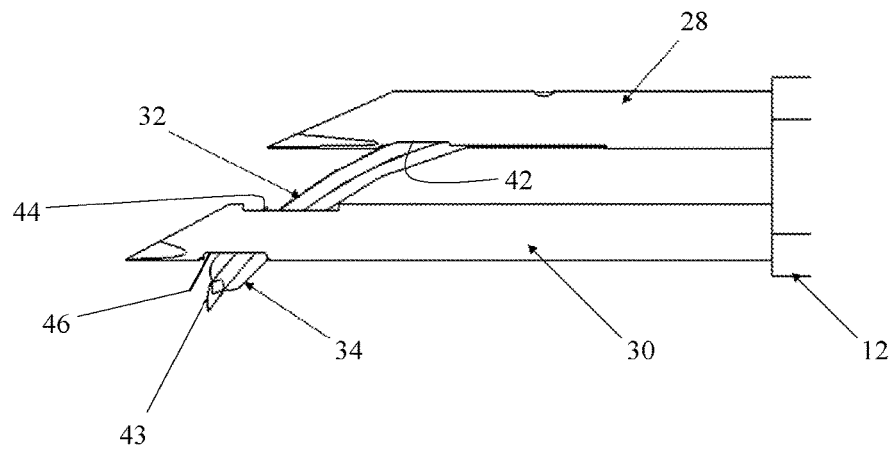
FIG. 6 is a detail plan view showing the portion of FIG. 5 which is denoted by the letter A.
Figure 8:
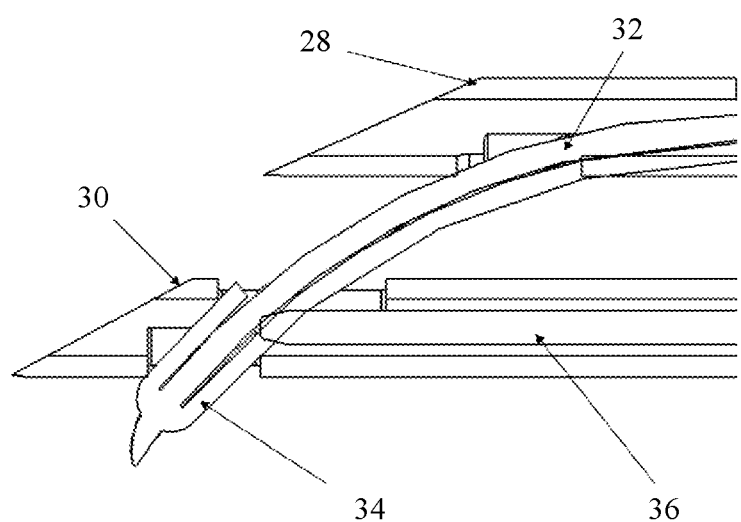
FIG. 8 is an enlarged plan view of the distal end of the meniscal repair device of the invention, illustrating the suture needle as it is driven from the transfer needle to the catch needle.

In FIGS. 6 and 8, the distal end of the meniscal repair device 10 is illustrated. The distal end of the device 10 comprises a transfer needle 28 and a catch needle 30. A suture needle 32 is extendable from the transfer needle 28, as shown in FIG. 6, for carrying suture 34 toward the catch needle 30 for purposes to be described below. A catch plunger 36 is also provided, as shown in FIG. 8.

Figure 3:
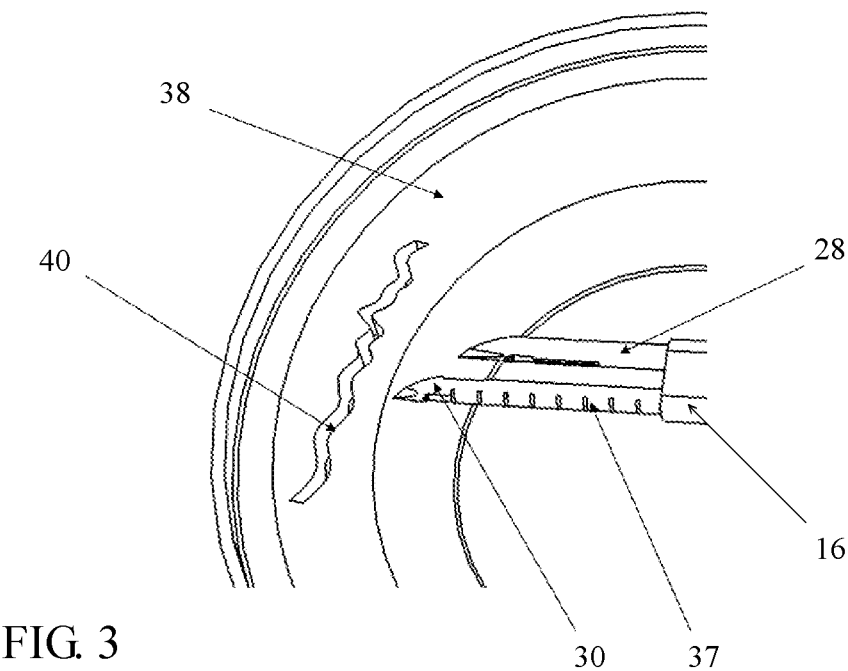
FIG. 3 is a plan view illustrating a distal end of the meniscal repair device illustrated in FIGS. 1 and 2 as it approaches a torn meniscus to be repaired.

Now, with reference to the drawing figures, a representative procedure which may be performed using the inventive device 10 will be described. As noted above, in FIG. 1 the device 10 is illustrated as it is configured prior to insertion into a patient. Once the practitioner has measured the depth from the needle insertion point to the approximate needle exit point, the device can be inserted into the patient's knee. The sheath 16 is retractable, and covers the transfer needle 28 and catch needle 30 while the device is introduced into the patient, for the purpose of protecting the patient from being injured by the needle points. The device 10 can be inserted into the patient's knee by any suitable means, such as a cannula or other type of introducer channel. Once the device 10 is inserted to the procedural site, the practitioner then retracts the sheath 16 by pulling the sheath actuation button 18 backwards, and lets the sheath stop at the desired depth of penetration, which is indicated by the sliding depth gauge 22 on the handle 12. Another depth gauge 37, with graduated markings corresponding to those on the depth gauge 22, is disposed on the distal end of the catch needle 30, as shown in FIG. 3. This depth gauge is visible arthroscopically during the course of the procedure.

Figure 4:
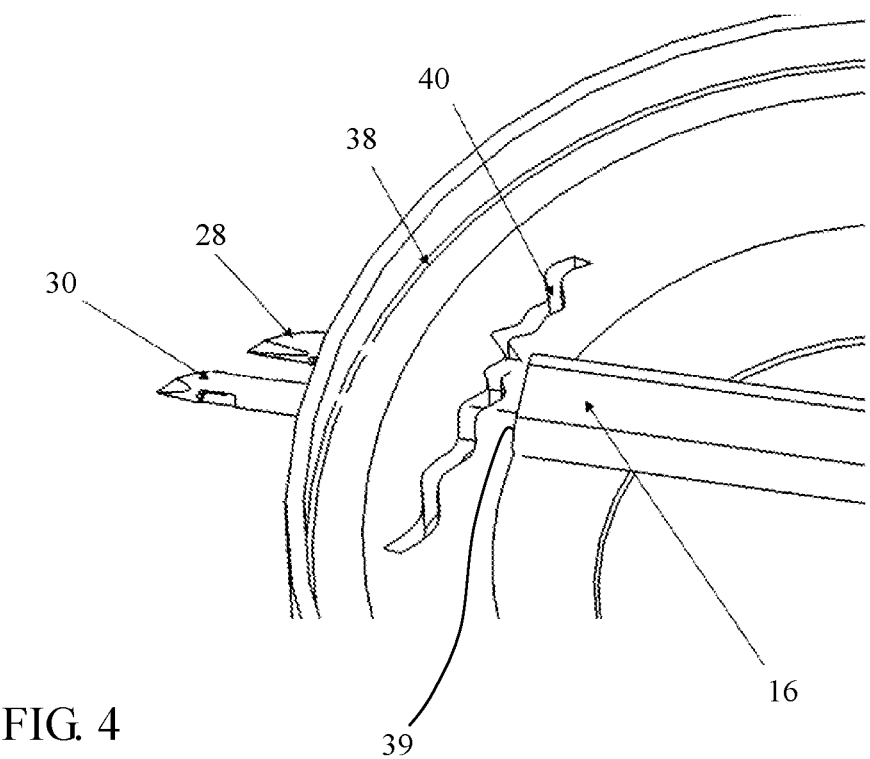
FIG. 4 is a plan view similar to FIG. 3, illustrating the distal end of the meniscal repair device after it has advanced into and through the meniscus.
Figure 5:
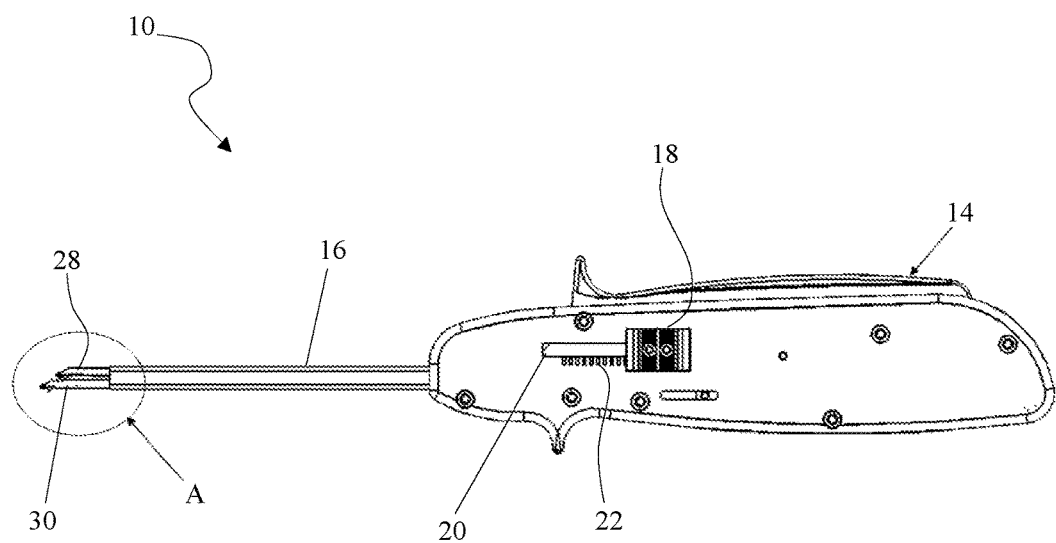
FIG. 5 is a plan view of the meniscal repair device of the present invention, showing the device as it is about to be actuated after the distal end has been positioned at the procedural site as shown in FIG. 4.

The practitioner continues to insert the device 10 until the sheath 16 comes into contact with the meniscus 38, at which point the device will be unable to go any deeper. This step of insertion is illustrated in sequential FIGS. 3 and 4. Note that in FIG. 4, distal progress of the device 10 has stopped, because the distal end 39 of the sheath 16 is in contact with the meniscus 38.

Once the needles 28 and 30 have been fully inserted through the meniscal tear 40 to be repaired, the practitioner then squeezes the suture needle advancement lever 14 downwardly toward the body of the handle 12. This action drives the suture needle 32 from the transfer needle 28 and into the catch needle 30, as shown in FIG. 6. The suture needle 32 exits the transfer needle 28 through a transfer needle window 42 and a distal end 43 of the suture needle 32 enters the catch needle 30 through a first suture catch window 44. As the suture needle 32 continues its travel, the distal end 43 thereof exits the catch needle 30 through a second suture catch window 46. In order to function in the described manner, the suture needle preferably has a needle point or piercing tip, as shown, configured to give it the ability to pierce through the meniscus 38, and is sufficiently flexible so that it can be housed in a straightened configuration inside the transfer needle 28 prior to actuation and then take the necessary bend during deployment. The suture needle 32 can be made of a spring tempered stainless steel or a shape memory type of alloy such as nitinol. It can be manufactured with processes that pre-shape it, thereby allowing it to be advanced out of the transfer needle 28 and into the catch needle 30.

Once the suture needle advancement lever 14 has been squeezed fully, the catch plunger 36 inside the catch needle 30 is actuated by releasing the catch spring piston 26 in the handle 12. A protrusion 48 on the suture needle advancement lever 14 hits the piston retention lever 24, which releases the catch spring piston 26 (FIG. 7). The catch spring piston 26 drives the catch plunger 36 toward the suture 34 and the suture needle 32. The catch plunger 36 advances distally sufficiently to collide with the suture 34 and pin the suture against the suture needle 32.

Figure 9:
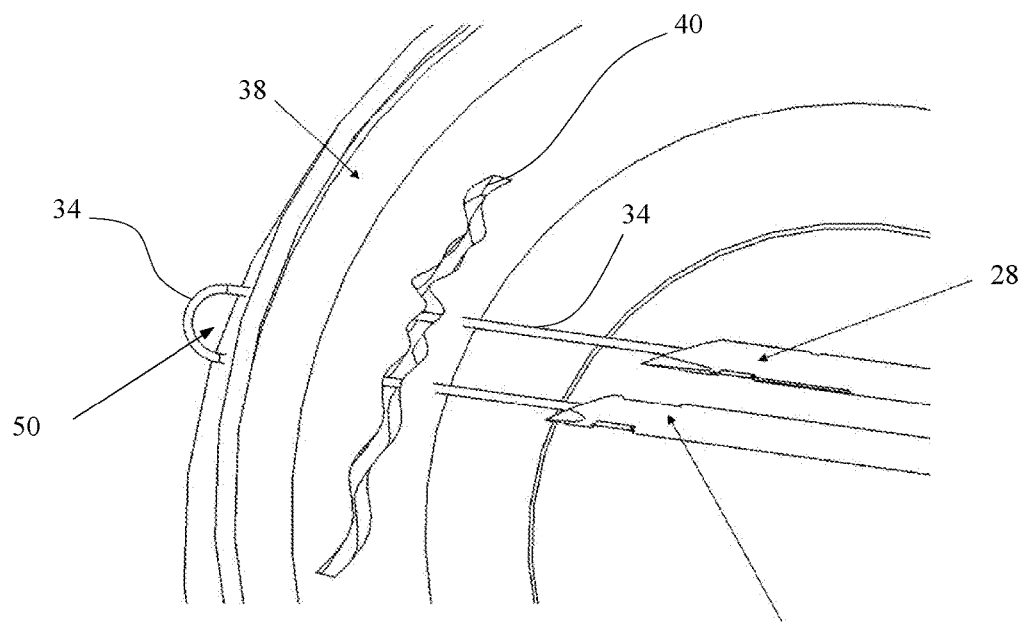
FIG. 9 is an isometric view illustrating the procedural site as the inventive device is withdrawn therefrom to loop the suture through the meniscus.

Releasing the suture needle advancement lever 14 retracts the suture needle 32, leaving the suture 34 behind inside of the catch needle 30. Once this step is completed, the device 10 is retracted from the patient. Since the suture 34 entered the patient attached to the transfer needle 28, and has now been passed to the catch needle 30, a suture loop 50, as shown in FIG. 9, has now been created through the meniscus 38.

Figure 10:
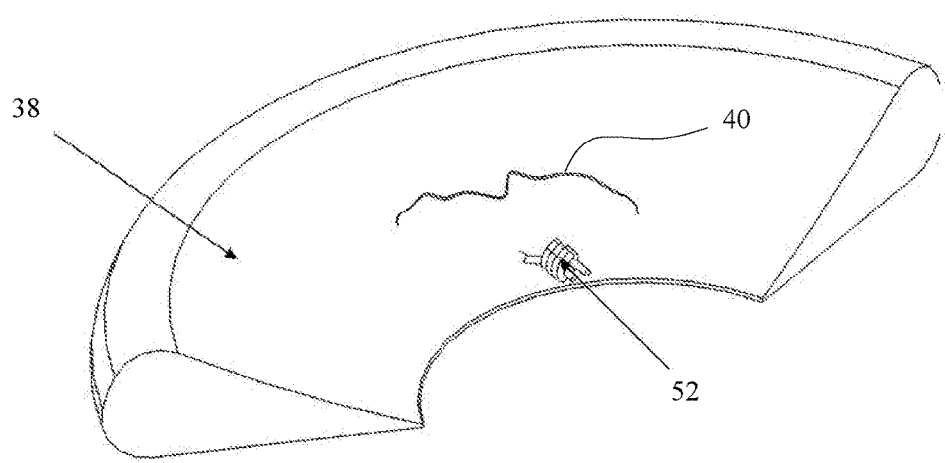
FIG. 10 is an isometric view showing the repaired meniscus after a pre-tied knot has been secured in place to stabilize the tear.

At this juncture, a pre-tied knot 52 is pulled tightly against the meniscus 38 and provides fixation for healing of the now closed meniscal tear 40. This pre-tied knot may be initially disposed on the instrument 10, and then slid down the suture legs 34 distally until it contacts the meniscus. The long ends of the suture 34, which extend proximally from the procedural site, are then cut off once the knot 52 is in place. The repaired meniscus 38 is shown in FIG. 10.

Figure 11:
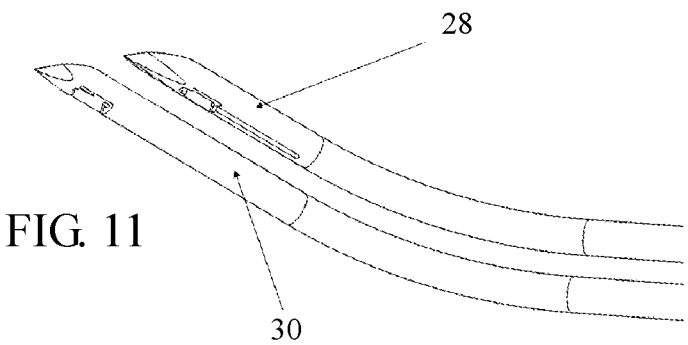
FIGS. 11-13 are views illustrating three different potential curve options for enhancing maneuverability of the inventive device.
Figure 12:
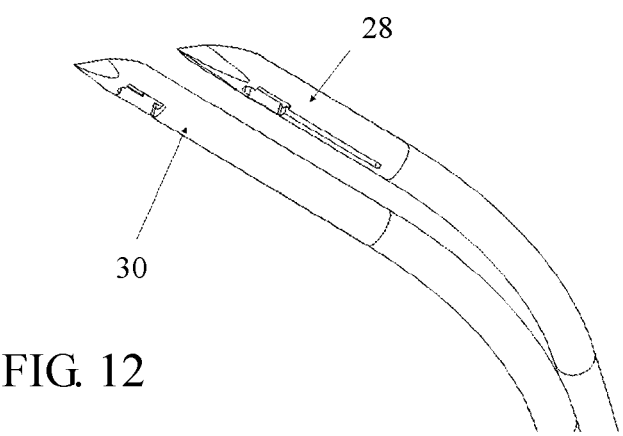
Figure 13:
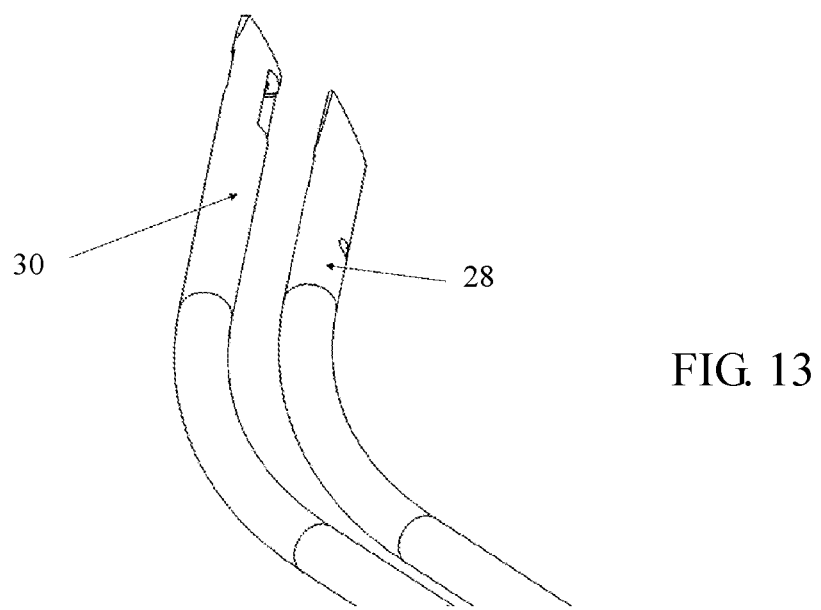

FIGS. 11-13 illustrate three alternative needle embodiments, wherein the transfer needle 28 and the catch needle 30 are curved, rather than straight, as in the embodiment illustrated in FIGS. 1-10. Curves of the type disclosed in FIGS. 11-13 may be used to facilitate maneuvering beneath the femoral condyles.

Currently, the curves being explored are fixed during the manufacturing process. The cavity between the femoral condyle and the meniscus can be quite tight, and as such, in some embodiments of the invention, it can be advantageous for the curves to be adjusted by the practitioner, as needed, to maneuver inside of the joint space.

The approach shown in the figures thus far involve a horizontal stitch placement. However, it is possible, and has been achieved by the inventor in cadaver tissue, to rotate the needle into a vertical position and to place the stitch. There are instances where this would be an advantageous approach from a repair strength standpoint.

The bevel orientation of the needles is currently fixed. However, the bevels can be changed in order to make the device easier to use.

The shield/depth limiter shown and described above is one approach with regards to limiting the insertion depth of the device into the meniscus.

Within the scope of the present invention, it is possible to add a tag or barb onto the end of the suture 34, which will provide a good piercing point, as an alternative to the current suture needle approach. A hard feature may also be employed, which makes capture of the suture easier and more resistant to letting go prematurely.

The device is not presently re-loadable in the operating room. However, in alternative embodiments, the device may be designed to be easily re-loadable.

The width of the stitch is an important factor in determining the strength of the final repair. Basically, the wider the stitch, the stronger the repair will be. The width of the stitch, in some invention embodiments, is adjustable in the operating room. This way the practitioner is able to determine the best stitch width for the given situation.

The bevel orientation of the needles is currently fixed. However, these may change in order to make the device easier to use.

The sheath/depth limiter described and shown is one alternative with regard to limiting the insertion depth of the device into the meniscus. In the present invention, there is a stationary steel component which joins the needles together and holds their orientation. This component can be made to slide along the axis of the needle. By doing this, it can be utilized for depth limitation.

Other adjustable depth limiting devices may include inflatable structures, absorbing cushions, ball detents, and metal crush sleeves, for examples.

A different depth limiting approach is to move the needles in and out of a stationary sheath which provides depth limiting. This way, the needles may be completely shrouded upon entering the patient without need for additional insertion sheaths.

Figure 14:
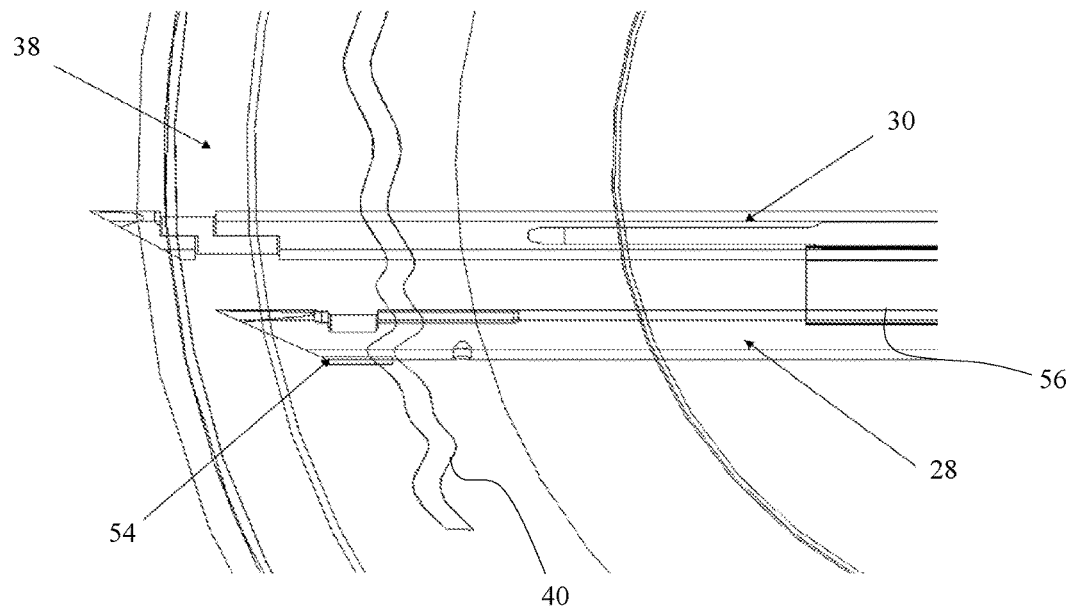
FIG. 14 is a plan view illustrating an alternative force feedback depth limitation feature for the present invention, wherein the plunger element is under compression.
Figure 15:
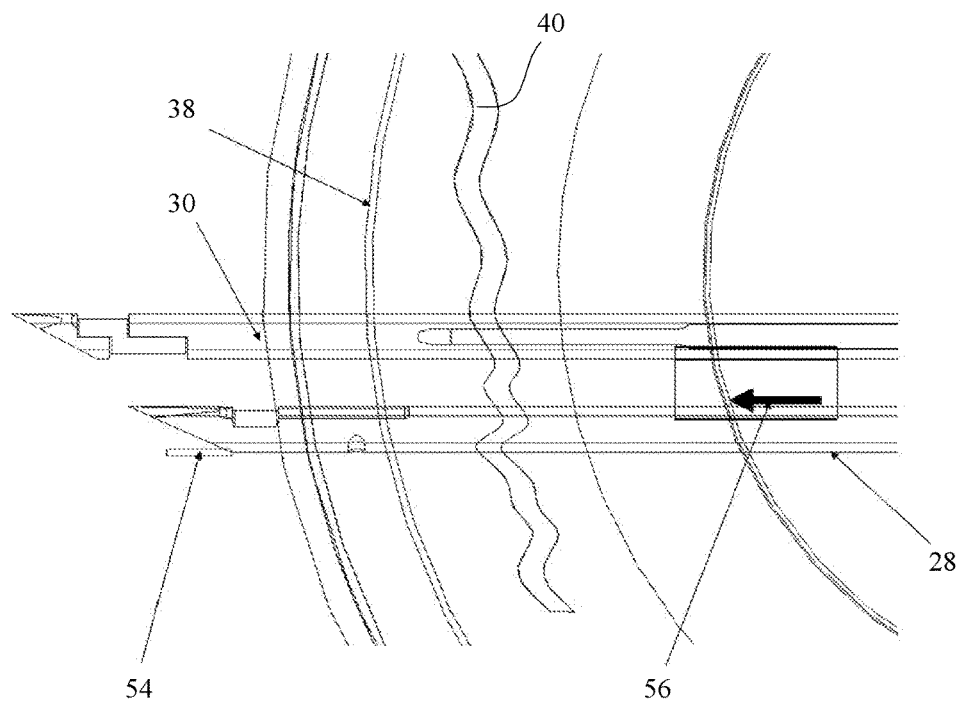
FIG. 15 is a plan view similar to FIG. 14, illustrating release of the plunger element upon exiting of the device from the distal end of the meniscus.

Still another approach is to utilize a method of force feedback to determine whether the needle tips have gotten past the outer surface of the meniscus and into the capsule. FIGS. 14 and 15 illustrate such a method sequentially. A compression force (plunger) element 54 may be placed on the distal end of the shorter transfer needle 28. When the plunger 54 exits the meniscus and enters the capsule, the force on the needle reduces, and the plunger then springs forward and releases a mechanism which drives a depth limiter 56 distally against the meniscus (FIG. 15) and thus prevents further distal penetration of the needles.

Now with reference particularly to FIGS. 16-22, an alternative embodiment of the suture, transfer, and catch needles is illustrated which results in significantly improved functionality. In this embodiment, like elements to those in prior embodiments are identified by like reference numerals, preceded by the numeral 1.

Figure 16:
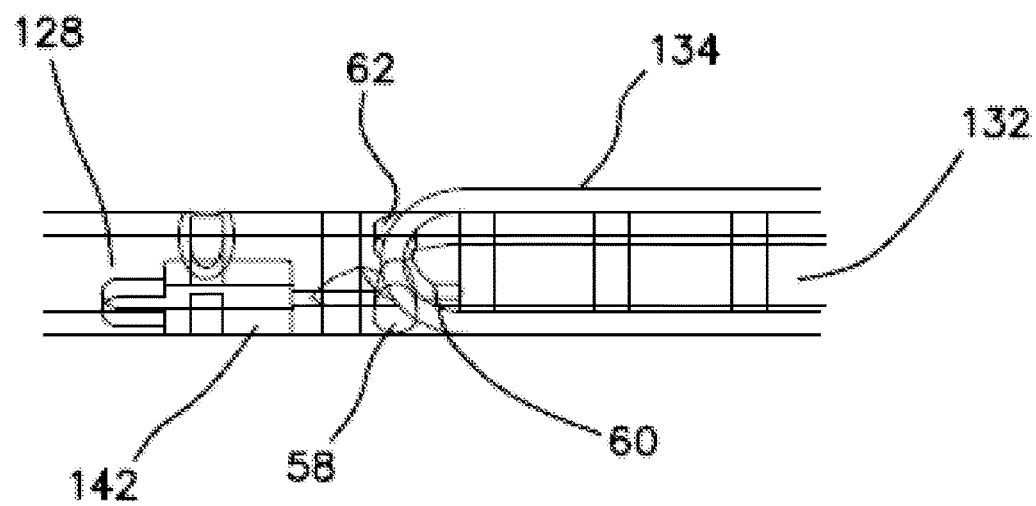
FIG. 16 is a detail view showing a modified embodiment of the suture needle and the transfer needle of the present invention.
Figure 17:
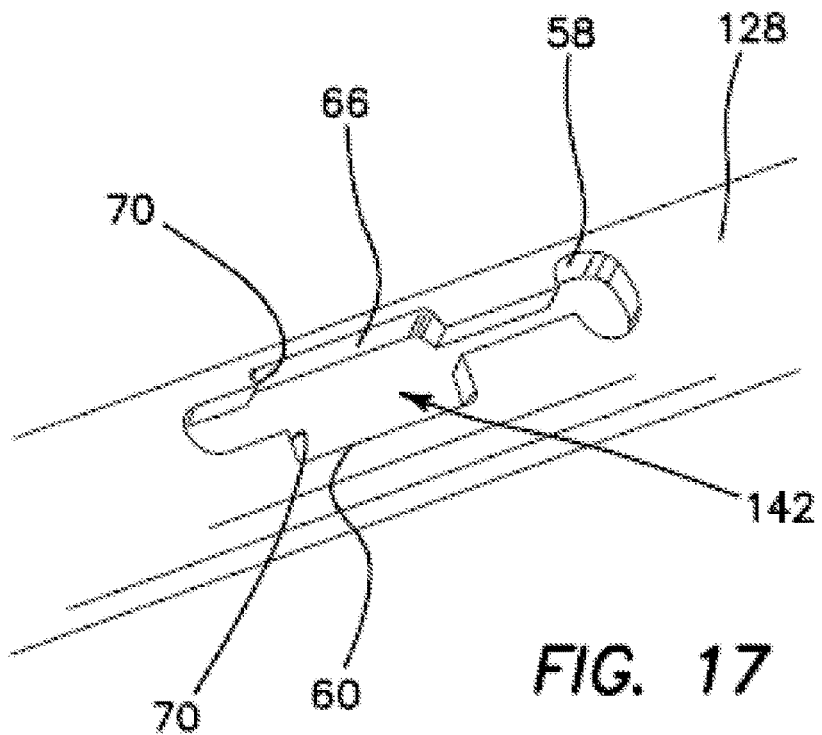
FIG. 17 is an isometric view showing the transfer needle of FIG. 16 and an innovative window disposed therein, for ensuring that the suture needle is properly aimed toward the catch needle.
Figure 18:
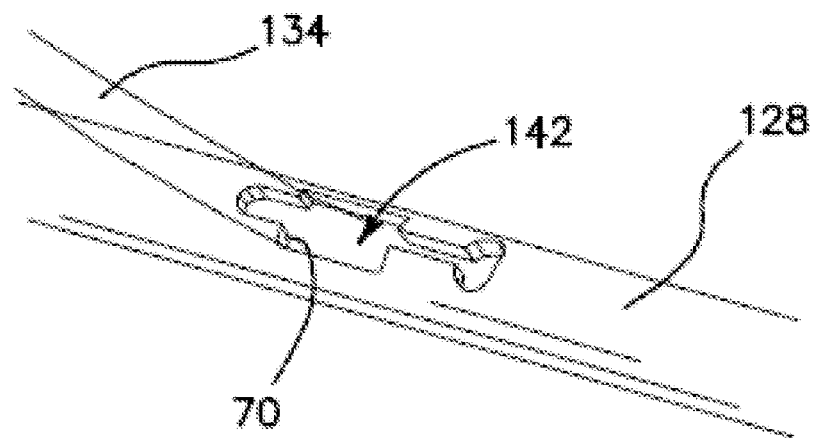
FIG. 18 is an isometric view of the embodiment of FIG. 16 showing the suture needle as it slides across and out of the transfer needle.

As shown in FIGS. 16 and 17, suture 134 is loaded through an open portion 58 of the wall of the transfer needle 128 into a hook 60 of the suture needle 132 disposed in a lumen 62 (FIG. 19) of the transfer needle 128, and through a hole 64 in an opposite wall of the transfer needle 128. The hook 60 of the suture needle 132 is then retracted within the lumen 62 to securely fasten the suture to the transfer needle 128.

Figure 19:
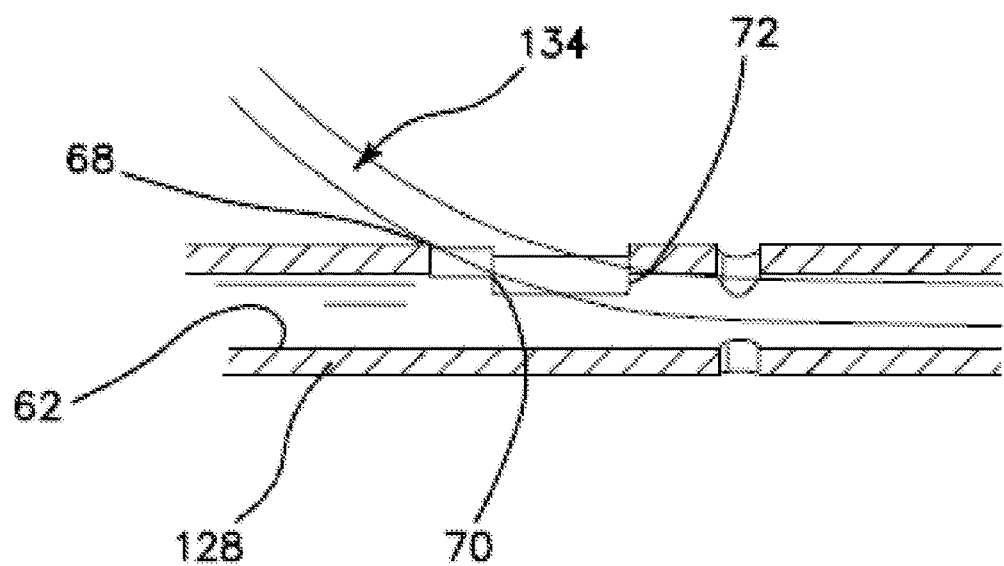
FIG. 19 is a plan view of the embodiment shown in FIG. 18.
Figure 20:
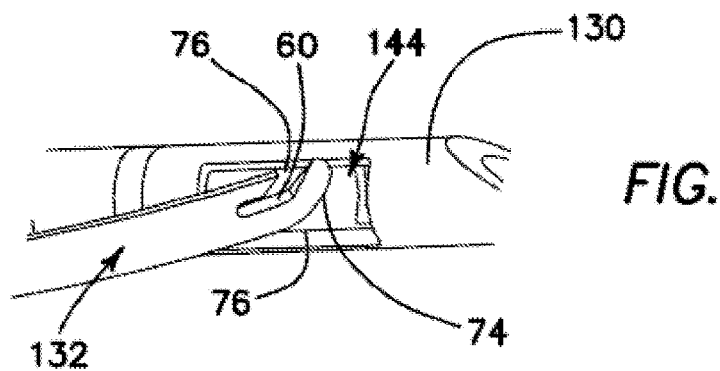
FIG. 20 is a view showing the suture needle of the FIG. 16 embodiment as it approaches the catch needle.
Figure 21:
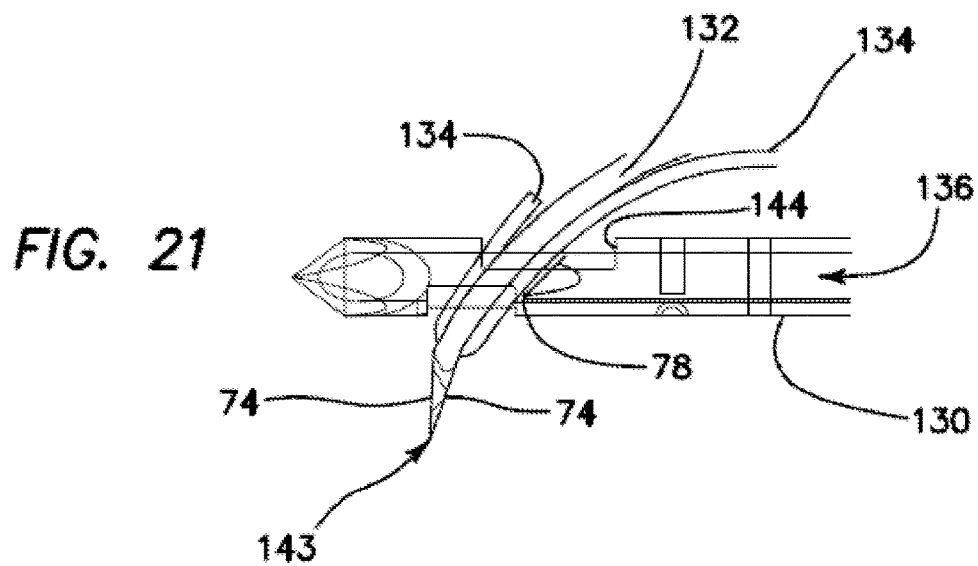
FIG. 21 is a plan view showing the suture and suture needle extending through the catch needle of the FIG. 16 embodiment.
Figure 22:
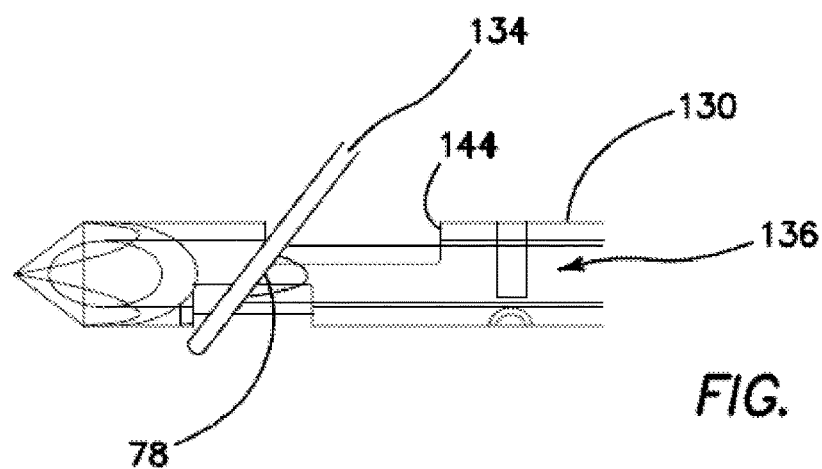
FIG. 22 is a plan view showing the suture retained in the catch needle after the suture needle has been withdrawn back into the transfer needle of the FIG. 16 embodiment.

The deflection of the suture needle 132 either by tissue or by torquing of the catch needle 130 and the transfer needle 128 can cause the suture needle 132 to miss the first suture catch window 144 in the catch needle 130. Several principle innovative features are advantageously employed to ensure that the suture needle 132 does not miss the first suture catch window 144. A first advantageous feature is that the transfer needle window 142 is cut with parallel sides 66 for the suture needle 132 to slide across in order to maintain the trajectory of the suture needle 132 parallel with the sides of the window 142. A second advantageous feature is that the suture needle 132 has a flat surface 68 (FIG. 19) that slides across a bearing surface 70 of the transfer needle window 142 which is substantially perpendicular to the path of the suture needle, thereby maintaining the trajectory of the suture needle 132. The length of the transfer needle window 142 is shorter than required to allow free translation of the needle 132 into and out of the window. The relatively short window length creates an interference zone 72 between the suture needle and the edge of the transfer needle window, as shown in FIG. 19, which interference forces the flat surface 68 of the suture needle 132 against the bearing surfaces 70 of the transfer needle window 142, perpendicular to the path of the suture needle, to further help maintain the trajectory of the suture needle.

The suture needle has angled surfaces 74 extending from the distal tip 143 of the needle, which are designed to slide and ramp on corresponding angled surfaces 76 in the window 144 of the catch needle 130, to allow the suture needle to have sufficient deflection to pass through the window 144.

The catch plunger 136 is also preferably designed with an angled distal surface 78 that is adapted to mate with a similarly angled surface 74 of the suture needle. This angled surface 78 allows for intimate contact with the suture needle, in order to pull off the suture from the hook 60 as the suture needle retracts.

Now with particular reference to FIGS. 23-37, there is shown a modified embodiment of the meniscal repair device 10, wherein like elements are designated by like reference numerals, preceded by the numeral 2. This device 210 is an integrated cannula and needle depth limiting system designed for the insertion of an arthroscopic device with a pre-tied knot into the joint space. The invention also reduces the friction during the actuation of passing returning of a suture delivery needle.

The integrated cannula and depth limiter allows for a single handed integrated insertion and delivery of a pre-tied suture construct into soft tissue. The rigidity of the suture needle required to pass a needle through tissue into a secondary needle is great, and adds significant frictional forces that prevent the return of the suture needle. The reduction of the frictional forces of the suture needle is required to maintain the rigidity of the suture needle.

The meniscal repair device 210 has an incorporated cannulated sheath 216 which is used as an introducer and depth limiter. The sheath 216 translates and locks forward to completely cover the dual needles 228 and 230, which allow the device to be placed through the skin without the use of a cannula. The sheath 216 also translates and locks backward to expose the needles 228 and 230, with the degree of exposure correlating to a distance indicated on the device.

Figure 23:
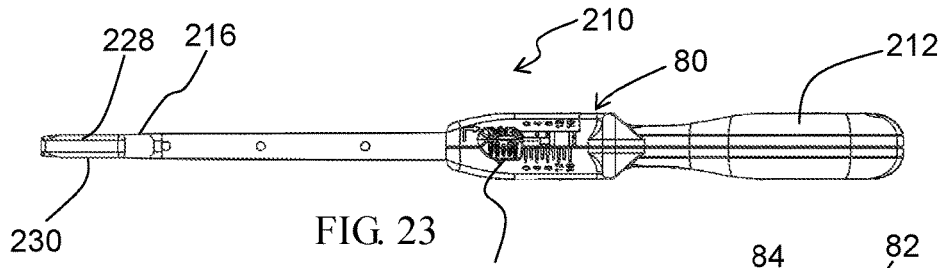
FIG. 23 is a top view of a modified embodiment of a meniscal repair device constructed in accordance with the principles of the present invention, illustrating a depth limiting feature wherein it is in a first fully extended configuration, with sheaths extended distally to completely cover the dual needles of the device.
Figure 24:
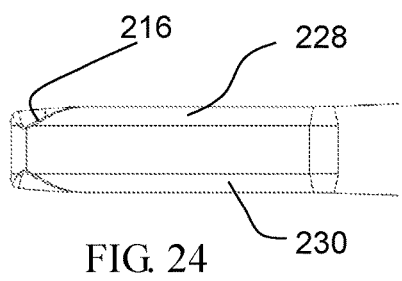
FIG. 24 is an enlarged view of the distal end of the device of FIG. 23.
Figure 25:
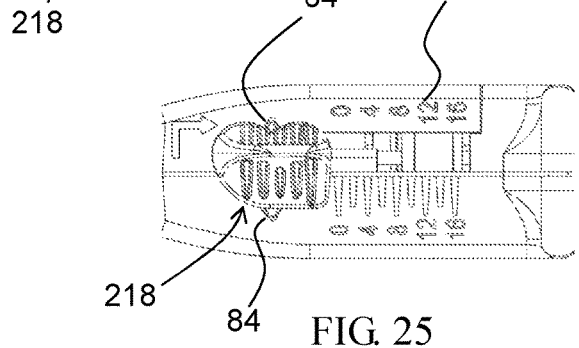
FIG. 25 is an enlarged view of the control portion of the device of FIG. 23.

FIGS. 23-25 illustrate the sheath 216 in its extended configuration, wherein it completely covers the dual needles 228 and 230. The device comprises a handle 212 on its proximal end, with a control portion 80 distally of the handle 212 for actuating the sheath 216 and the suture needle 232. The control portion 80 comprises a sheath actuator 218 which is movable axially to retract and extend the sheath. A numbered scale or depth gauge 82 is provided which is calibrated to correspond to the distance traversed by the sheath 216 when actuated. A pointer 84 on the actuator 218 indicates the numerical distance to which the sheath has been displaced. As shown in FIG. 25, the pointers 84 are distal to the zero on the depth gauge, which forward setting corresponds to full extension of the sheath 216 over the dual needles, as shown in FIGS. 23 and 24. This setting also may be identified as the "locked forward" configuration.

Figure 26:
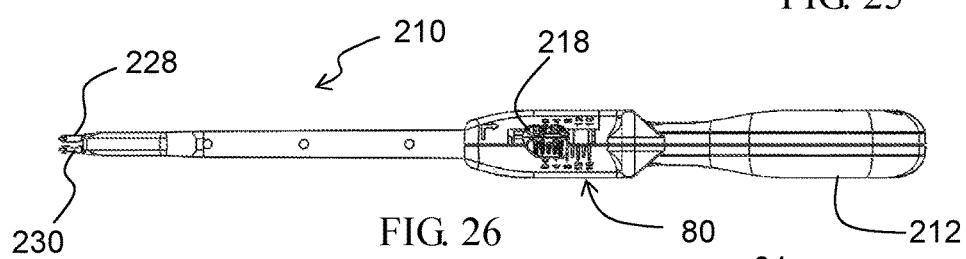
FIG. 26 is a top view of the device of FIG. 23, wherein the device is in an intermediate configuration, with the distal ends of the dual needles partially exposed.
Figure 27:
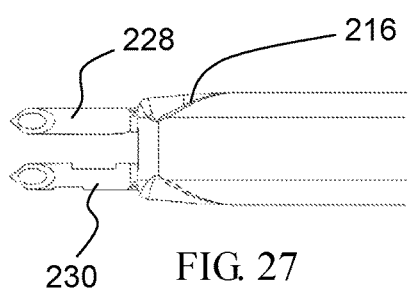
FIG. 27 is an enlarged view of the distal end of the device of FIG. 26, similar to FIG. 23.
Figure 28:
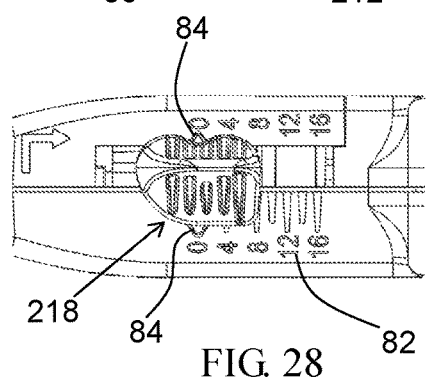
FIG. 28 is an enlarged view of the control portion of the device of FIG. 26, similar to FIG. 25.
Figure 29:
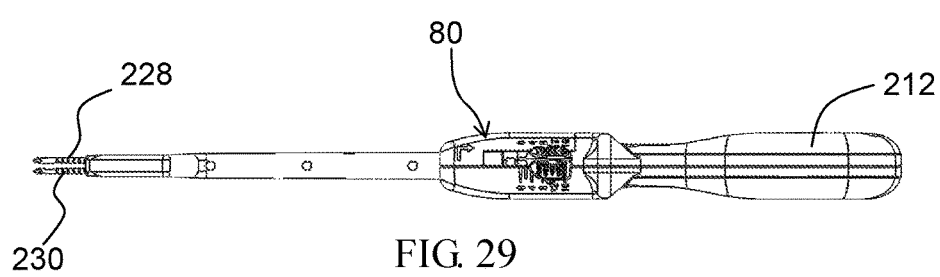
FIG. 29 is a top view of the device of FIGS. 23 and 26, wherein the device is in a fully retracted configuration, wherein the sheaths are fully retracted to completely expose the dual needles of the device.
Figure 30:
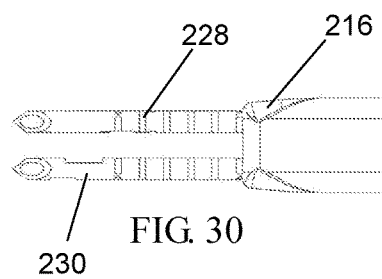
FIG. 30 is an enlarged view of the distal end of the device of FIG. 29, similar to FIGS. 23 and 27.
Figure 31:
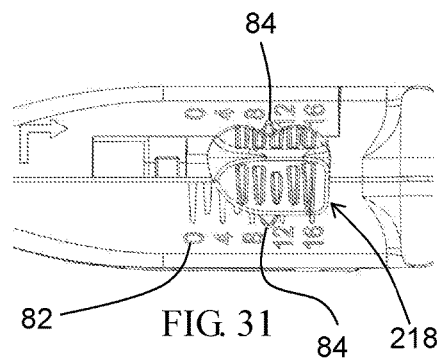
FIG. 31 is an enlarged view of the control portion of the device of FIG. 29, similar to FIGS. 25 and 28.

In FIGS. 26-28, the actuator 218 has been moved axially in a proximal direction, so that the pointers 84 indicate the setting corresponding to about 0 on the depth gauge 82. As can be seen in FIGS. 26 and 27, in this configuration, the sheath 216 has been retracted sufficiently so that the dual needles are partially uncovered. In FIGS. 29-32, the sheaths are in their fully retracted, or locked backward configuration, so that the dual needles are fully exposed. This configuration, in the illustrated embodiment, corresponds to a setting of about 10 on the depth gauge, as shown in FIG. 31.

In this embodiment, anything not particularly discussed herein may be assumed to be substantially the same as in the prior disclosed embodiment. For example, a suture needle advancement and retraction control is provided on the control portion 80, though it is not specifically shown.

Figure 32:
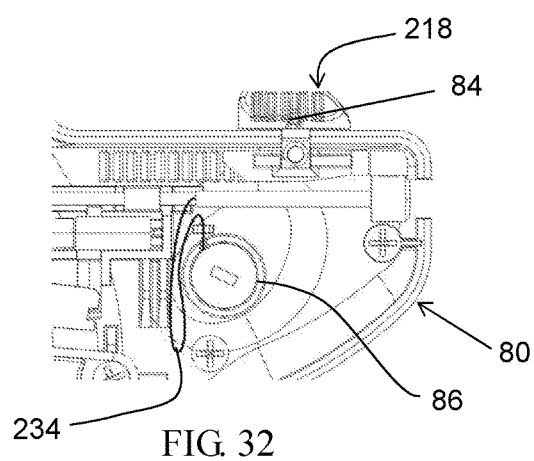
FIG. 32 is a side cross-sectional view showing suture slack within the handle of the device as a suture knot resides beneath the sheath, ready for deployment.
Figure 33:
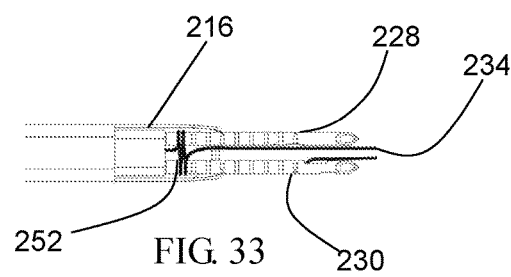
FIG. 33 is a view of the distal end of the device showing the pre-tied knot disposed beneath the sheath.
Figure 34:
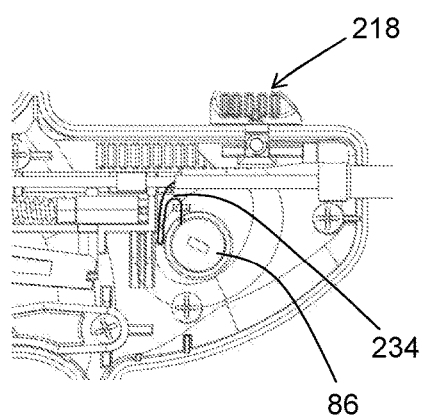
FIG. 34 is a view similar to FIG. 32, showing reduction in the slack in the suture within the handle after the knot has moved out from beneath the sheath and is traversing distally over the needles.
Figure 35:
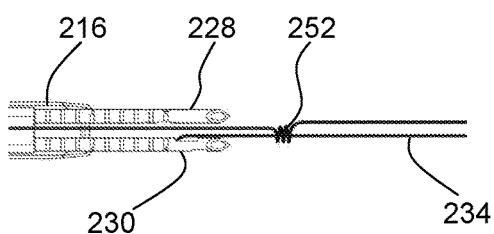
FIG. 35 is a view similar to FIG. 33 showing the knot after it has moved distally of the needles.
Figure 36:
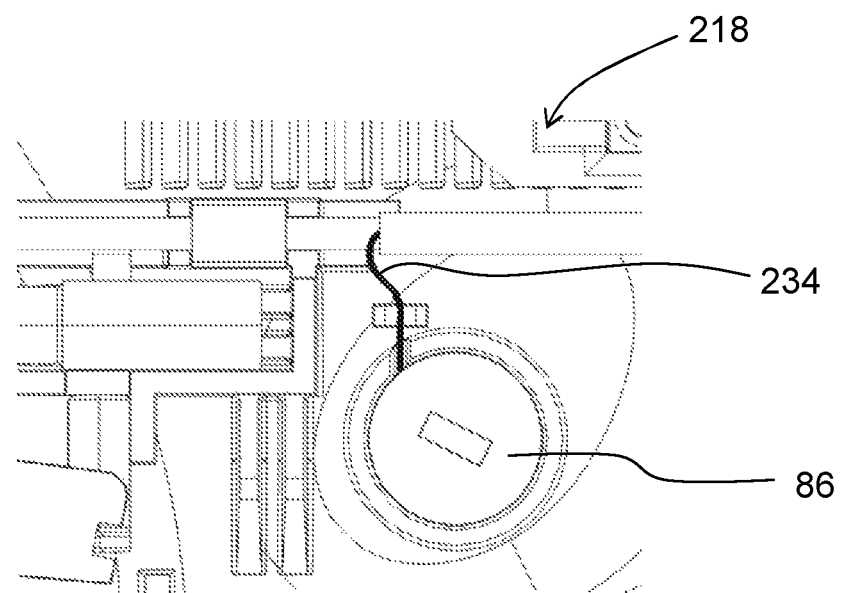
FIG. 36 is a view similar to FIGS. 32 and 34 showing the suture within the handle after all of the slack has been take out of the suture.
Figure 37:
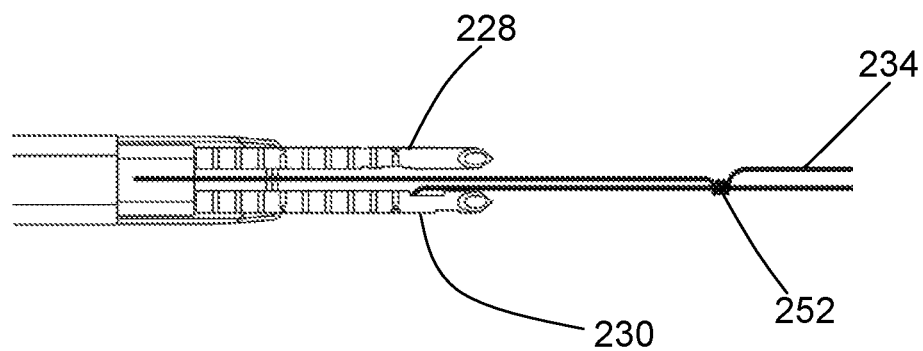
FIG. 37 is a view similar to FIGS. 33 and 35 showing the knot in a position to be tensioned against the tissue.

As shown in FIGS. 32-33, a pre-tied knot 252 is placed around the needles 228, 230 and covered by the sheath 216 during suture passing. A cleat 86 within the control portion housing 80 accommodates a length of suture 234 having considerable slack. When the device is pulled outside of the joint space, the knot 252 slides over the needles 228, 230 and out from underneath the sheath 216, as shown In FIGS. 34-35. As the knot 252 advances distally and slides off the needles, the slack in the locking end of the suture, within the housing 80, is reduced, as illustrated. Tension is then applied by the cleat 86 in the housing 86 and then released. This tightens down the knot 252 over the post end of the suture 234 (FIGS. 36-37) to allow the knot to slide down the post without capturing soft tissue, as it travels through the skin into the repair site.

The dual needles 228, 230 and the suture needle 232 are relatively rigid, which is important for reliably passing and capturing suture. However, the stiffness of the nitinol suture needle causes significant friction that can result in difficulty of the suture needle to fully retract into the transfer needle. This friction is also increased when the dual needles are in a curved configuration (FIGS. 11-13). To reduce the friction between the nitinol suture needle and the stainless steel transfer needle, an oxide layer infused with Tungsten Disulfide is formed. This significantly reduces the friction, and allows for more complex curves to be manufactured.

Of course, while the foregoing invention has been disclosed in connection with the repair of meniscal tissue, it will be recognized that the inventive principles are applicable to many other instances wherein it is desired to repair a tear in a portion of soft tissue.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A device for repairing a tear in a portion of tissue, comprising:
   a proximal actuator portion;

a transfer needle extending distally from the proximal actuator portion and having a distal tip for piercing tissue;

a catch needle extending distally om the proximal actuator portion and having a distal tip for piercing tissue;

a suture needle disposed within a lumen in said transfer needle, said suture needle being extendable from said transfer needle toward said catch needle and retractable from said catch needle toward said transfer needle; and a window disposed on said transfer needle, through which said suture needle may be deployed, said window having two substantially parallel sides and a bearing surface which is disposed substantially perpendicularly to a path of the suture needle as the suture needle traverses into and out of said window;

wherein said window has a length that is shorter than required to permit free translation of the suture needle into and out of the window, so that an interfering contact is created between a first surface of the suture needle and the edge of the transfer needle window; and wherein said suture needle comprises a second surface thereof which is substantially flat and on an opposing side of the suture needle relative to the first surface, so that the interfering contact between the first suture needle surface and the edge of the transfer needle window causes the substantially flat second suture needle surface against the transfer needle bearing surface.

2. The device as recited in claim 1, and further comprising a suture catch window in said catch needle for receiving said suture needle into the catch needle.

3. The device as recited in claim 2, wherein said suture needle comprises angled surfaces extending from a distal tip thereof, and said suture catch window also comprises angled surfaces, and further wherein the suture needle angled surfaces and the suture catch window angled surfaces are configured to correspond to one another so that the suture needle slides and ramps along the suture catch window angled surfaces to assist in guiding the suture needle into and out of the suture catch window.

4. The device as recited in claim 3, and further comprising an extendable catch plunger disposed in said catch needle for capturing suture therein when it is transferred from said transfer needle, wherein said catch plunger comprises an angled distal surface which is configured to mate with a corresponding one of said angled suture needle surfaces.

5. The device as recited in claim 2, and further comprising a second window disposed on said catch needle on a side opposed to the side on which the first window is disposed, through which a distal end of the suture needle extends when the suture needle is fully extended into the catch needle.

6. The device as recited in claim 1, and further comprising a retractable insertion sheath for covering the transfer needle and the catch needle when the device is inserted into a procedural site, wherein said proximal actuator portion comprises an insertion sheath actuator for retracting and advancing said insertion sheath.

7. The device as recited in claim 6, and further comprising a depth limiting apparatus for limiting the depth of insertion of said needles into the procedural site which is integrated with said insertion sheath actuator.

8. The device as recited in claim 7, wherein said depth limiting apparatus comprises a depth gauge disposed on said proximal actuator portion.

9. The device as recited in claim 8, wherein said insertion sheath actuator comprises a button which slides axially along a slot in said proximal actuator portion, said depth gauge comprising graduated numbered markings disposed along said slot, so that a practitioner can retract said sheath by sliding the insertion sheath actuator button to a selected position along said slot to control the depth of insertion of said device, between a locked forward configuration and a locked backward configuration.

10. The device as recited in claim 6, and further comprising a cleat disposed within said proximal actuator portion which is attached to a length of suture extending from the proximal actuator portion and having a pre-tied knot thereon, the cleat being configured to selectively apply tension to the suture.

11. The device as recited in claim 10, wherein prior to deployment the pre-tied knot is disposed beneath said sheath and there is a substantial length of slack suture within said proximal actuator portion.

12. The device as recited in claim 11, wherein the pre-tied knot slides distally over the needles and length of suture when the device is pulled proximally away from the procedural site, with the slack suture attached to the cleat simultaneously being reduced.

13. The device as recited in claim 1, wherein an oxide layer infused with tungsten disulfide is formed between the suture needle and the transfer needle to reduce friction therebetween.

14. The device as recited in claim 13, wherein the suture needle is comprised of nitinol and the transfer needle is comprised of stainless steel.

15. A device for repairing a tear in a portion of tissue, comprising:

a proximal actuator portion;

a needle for dispensing suture into the tissue to be repaired;

a retractable insertion sheath for covering the needle when the device is inserted into a procedural site; and a cleat disposed within said proximal actuator portion which is attached to a length of suture extending from the proximal actuator portion and having a pre-tied knot thereon, the cleat being configured to selectively apply tension to the suture.

16. The device as recited in claim 15, wherein prior to deployment the pre-tied knot is disposed beneath said sheath and there is a substantial length of slack suture within said proximal actuator portion.

17. The device as recited in claim 15, wherein the pre-tied knot slides distally over the needles and length of suture when the device is pulled proximally away from the procedural site, with the slack suture attached to the cleat simultaneously being reduced.

18. A device for repairing a tear in a portion of tissue, comprising:

a proximal actuator portion;

a transfer needle extending distally from the proximal actuator portion and having a distal tip for piercing tissue;

a catch needle extending distally from the proximal actuator portion and having a distal tip for piercing tissue;

a suture needle disposed within a lumen in the transfer needle, the suture needle being extendable from the transfer needle toward the catch needle and retractable from the catch needle toward the transfer needle, the suture needle including first and second opposed surfaces; and a window disposed on the transfer needle including a proximal edge, a distal edge, and two substantially parallel sides, the window structured to allow passage of a portion of the suture needle therethrough, the distal edge of the window defining a bearing surface which is disposed substantially perpendicularly to a path of the suture needle as the suture needle traverses into and out of the window, the proximal edge of the window defining an interference surface;

wherein the window has a length that is shorter than required to permit free translation of the suture needle into and out of the window, so that an interfering contact is made between the first surface of the suture needle and the interference surface of the window, and a bearing contact is made between the second surface of the suture needle and the bearing surface of the window.

* * * * *

UNITED STATES PATENT AND TRADEMARK OFFICE
CERTIFICATE OF CORRECTION

PATENT NO. : 10,335,140 B2
APPLICATION NO. : 15/273429
DATED : July 2, 2019
INVENTOR(S) : Baird et al.

Page 1 of 1

It is certified that error appears in the above-identified patent and that said Letters Patent is hereby corrected as shown below:

In the Claims

Column 13, Line 4, in Claim 1, delete "om" and insert --from-- therefor

Signed and Sealed this
Thirtieth Day of June, 2020

Andrei Iancu
*Director of the United States Patent and Trademark Office*